United States Patent [19]

Yamamoto et al.

[11] Patent Number: 4,826,879

[45] Date of Patent: May 2, 1989

[54] INTRAOCULAR PRESSURE LOWERING COMPOSITION FOR TOPICAL USE

[75] Inventors: Yujiro Yamamoto, Suita; Takahiro Ogawa, Nishinomiya; Yoshikazu Kuribayashi, Kobe, all of Japan

[73] Assignee: Senju Pharmaceutical Co., Ltd., Osaka, Japan

[21] Appl. No.: 3,285

[22] Filed: Jan. 14, 1987

[30] Foreign Application Priority Data

Jan. 31, 1986 [JP] Japan .................................. 61-20361

[51] Int. Cl.$^4$ ............................................ A61K 31/135
[52] U.S. Cl. ..................................... 514/657; 514/913
[58] Field of Search ................................. 514/657, 913

[56] References Cited

U.S. PATENT DOCUMENTS 4,010,202  3/1977  Sugihara et al. ..................... 514/657
4,035,512  7/1977  Sugihara et al. ..................... 514/657

OTHER PUBLICATIONS

Chem. Abst. 85: 20935s (1976)–Sugihara et al.
Chem. Abst. 89: 75331(e) (1978)–Sugihara et al.

Primary Examiner—Douglas W. Robinson
Attorney, Agent, or Firm—Wenderoth, Lind & Ponack

[57] ABSTRACT

An ocular antihypertensive composition for topical use which contains an effective amount of a compound represented by the formula

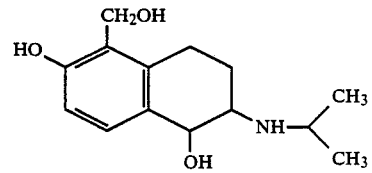

or a salt thereof having, in low concentrations, intraocular pressure lowering activity in mammals, low toxicity and no influence on the pupil size and, therefore, is useful as a therapeutic agent for glaucoma, for instance.

Furthermore, since the compound is effective in low concentrations, the possibility of tolerance development is considered to be scarce.

6 Claims, 5 Drawing Sheets

INTRAOCULAR PRESSURE LOWERING COMPOSITION FOR TOPICAL USE

BACKGROUND OF THE INVENTION

1. Field of the Invention

This invention relates to an ocular antihypertensive composition for topical use which contains an effective amount of a compound of the formula

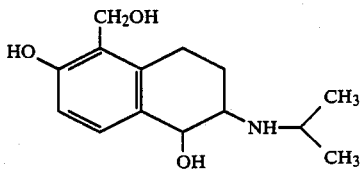

or a salt thereof.

2. Description of the Prior Art

Heretofore various drugs have been used for the purpose of inhibiting intraocular pressure increase or lowering increased intraocular pressure. Thus, epinephrine, for instance, is known as an ocular antihypertensive agent. When epinephrine is used in patients with narrow-angle glaucoma, however, it intensifies angle closure because of its mydriatic activity and may possibly cause acute intraocular pressure rise and, furthermore, blood pressure increase and/or conjunctival pigmentation is often observed.

Parasympathomimetic drugs such as pilocarpine induce visual field deterioration or abnormal accomodation, among others.

Beta-blockers such as timolol, which are recently in wide use in the treatment of glaucoma, are reported to produce adverse systemic effects, inducing bradycardia, heart failure, asthmatic attack, etc. Therefore, beta-blockers cannot be used in patients with such symptoms.

On the other hand, beta-stimulators are expected to be usable also in such patients. However, salbutamol, which is a conventional beta-stimulator, can produce a satisfactory effect only when it is used in high concentrations in which it might cause marked conjunctival hyperemia. Therefore, salbutamol is said to be unsuited for prolonged administration.

As mentioned hereinabove, a drug which would be effective in low concentrations in the prevention or treatment of increased intraocular pressure, typically in glaucoma, with the slightest adverse effects has not been available as yet. Accordingly, the present inventors attempted a search for an agent which would be safe and have satisfactory intraocular pressure-lowering activity.

The present inventors conducted an intensive research to develop a compound which would be effective at low concentration and be free of the above-mentioned disadvantages, and have ultimately accomplished the present invention.

SUMMARY OF THE INVENTION

The present invention is concerned with an ocular antihypertensive composition for topical use comprising an effective amount of a compound of the formula

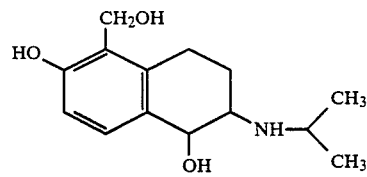

or a salt thereof.

DETAILED DESCRIPTION OF THE INVENTION

Figure 1:
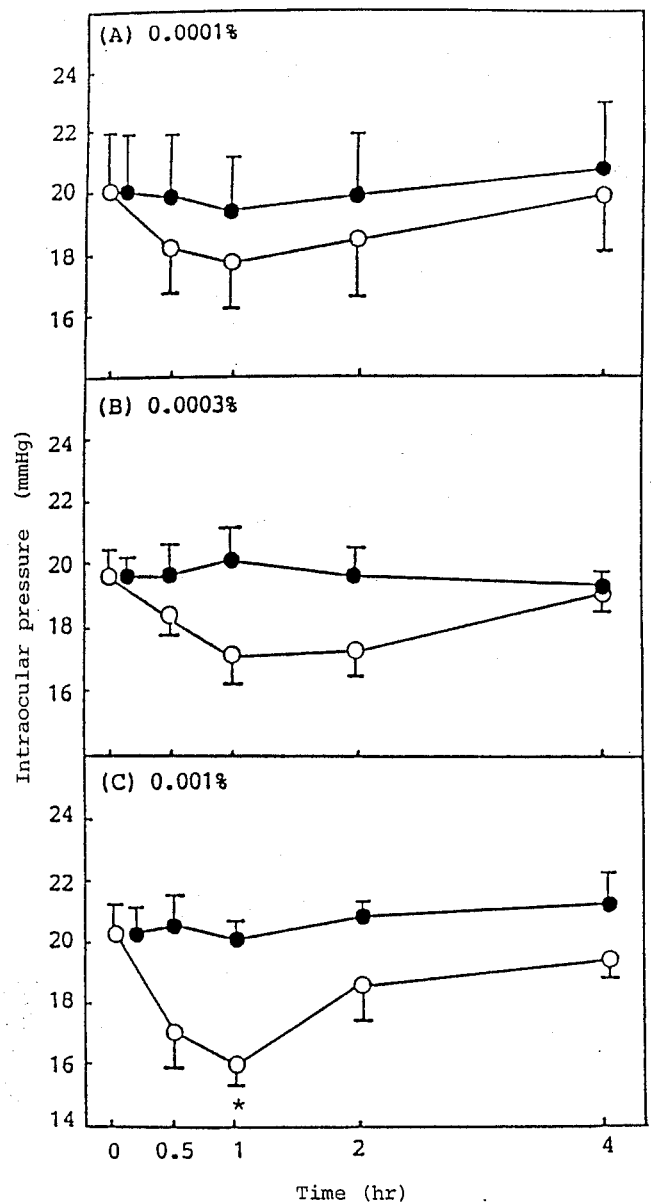
FIG. 1, FIG. 2 and FIG. 3 show the results of the tests for intraocular pressure lowering activity as conducted in the test example.

The ocular antihypertensive composition for topical use according to the present invention comprises the above compound or salt as an active ingredient thereof. The salt may be an inorganic salt such as hydrochloride, sulfate, nitrate, etc. or an organic acid salt such as oxalate, citrate, etc. In terms of solubility in water, the hydrochloride is preferred. This compound can be produced by the method described in U.S. Pat. No. 4,035,512, for instance. The compound of this invention may be used in trans-form, cis-form or their mixture, and particularly trans-form is preferred.

The above compound included as an active ingredient in the ocular antihypertensive composition for topical use according to the present invention has activity to lower the intraocular pressure of mammalian animals at low concentration, is low in toxicity, and has no influence on pupil size and, therefore, can be used advantageously in the pharmacotherapy for glaucoma.

The ocular antihypertensive composition according to the present invention is preferably manufactured in dosage forms suitable for local administration, such as eye-drops and ophthalmic ointment.

The eye-drops preferably contain the active compound in a concentration of 0.0001 to 1.0 percent, preferably 0.001 to 0.1 percent in an aseptic aqueous medium. The pH of the eye-drops of this invention is about 4–10, preferably about 5–9. For administration, one to a few drops per dose is instilled in the eye with a frequency of 1 to about 4 times a day according to the patient's condition. Such eye-drops may further contain pharmacologically acceptable addenda such as buffers for pH adjustment, e.g. phosphate buffer, borate buffer, citrate buffer, tartrate buffer and acetate buffer; isotonizing agents, e.g. sorbitol, glycerol, polyethylene glycol, propylene glycol, glucose and sodium chloride; preservatives, e.g. parahydroxybenzoic acid esters, benzyl alcohol, para- chloro-meta-xylenol, chlorocresol, phenethyl alcohol, sorbic acid, sorbic acid salts, thimerosal and chlorobutanol; chelating agents, e.g. edetate sodium and condensed sodium phosphate; and thickening agents e.g. carboxypropylcellulose, hydroxyethylcellulose, hydroxypropylcellulose, polyvinyl alcohol and sodium polyacrylate.

An eye ointment is produced by admixing the active ingredient in a concentration of about 0.0001–1.0%, preferably about 0.001–0.1%, with a conventional eye ointment base. The eye ointment is administered 1 to about 4 times a day depending on the patient's condition. As the eye ointment base, there may be mentioned petrolatum, Macrogol and carboxymethylcellulose sodium, among others.

In each dosage form, the ocular antihypertensive composition according to the invention may contain any other pharmacologically active ingredients unless they are unsuited for the purpose of the present invention.

The test results given below are illustrative of the effect of the ocular antihypertensive composition according to the invention. In the test, trans-2,5-dihydroxy-6-isopropylamino-5,6,7,8-tetrahydro-1naphthylmethanol hydrochloride (hereinafter referred to as "the Compound") was used.

EXPERIMENTAL EXAMPLE

The ocular antihypertensive effect of this compound was evaluated in male white rabbits weighing about 2 kg and having no ocular abnormality. The animals were kept in a vivarium controlled at 20°–28° C. and 40–70% R.H. Food intake was restricted, while water was made available ad libitum.

The test substance was dissolved in 20 mM phosphate buffer to concentrations of 0.0001, 0.0003, 0.001, 0.003, 0.01, 0.03, and 0.1%. The pH of the solutions was adjusted to 7.0–7.2 and the osmotic pressure to about 300 mOsm/kg.H$_2$O.

Four animals were used. Fifty microliters of each test substance solution was instilled into one eye and 50 μl of phosphate buffer adjusted to pH 7.0–7.2 and about 300 mOsm/kg.H$_2$O (osmotic pressure) into the fellow eye.

Immediately before and 0.5, 1, 2 and 4 hours (6 and 8 hrs. for 0.03% and higher concentrations) after instillation, the intraocular pressure was measured with a PTG (pneumatograph, Alcon) and the pupillary diameter was measured with a Mita universal gauge. Prior to measurement, a local anesthetic (0.4% Anelocal Eyedrops, Senju Pharmaceutical Co. Ltd.) was instilled into the eyes.

Figure 2:
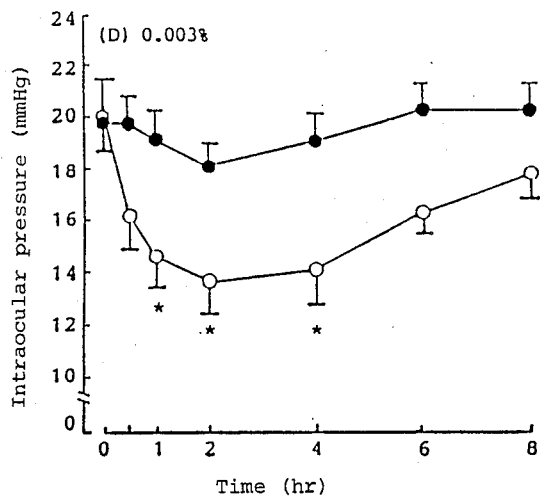
Figure 2:
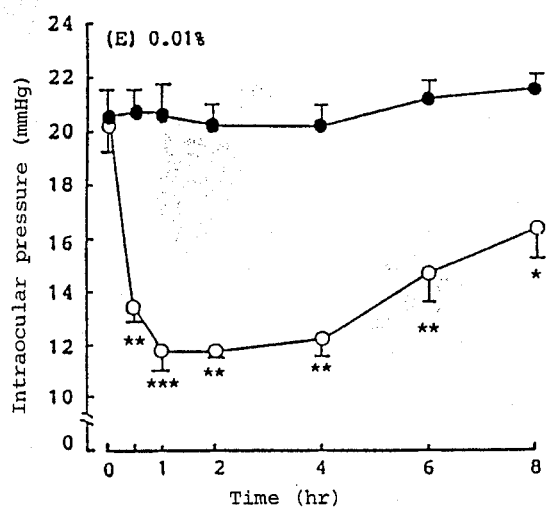
Figure 3:
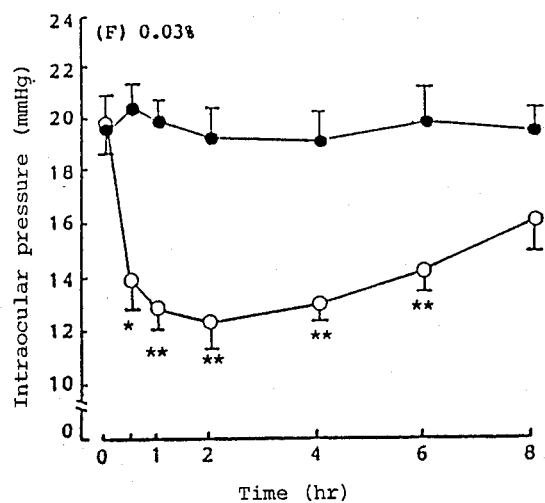
Figure 3:
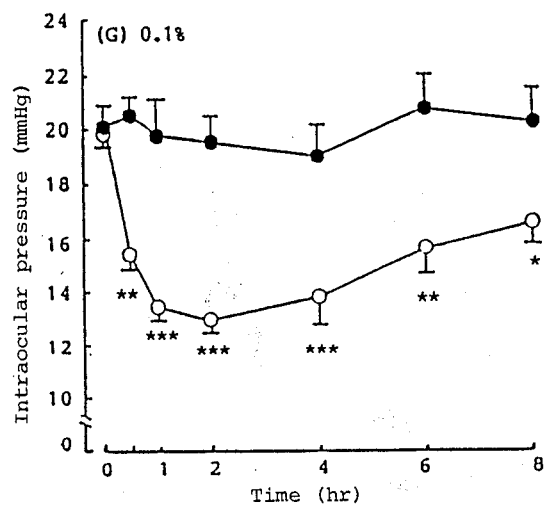

The intraocular pressure lowering effects thus produced are shown in FIGS. 1–3. In FIGS. 1–3, the data represented by open circles are for Compound, those by solid circles are for the base composition. The marks *,  and * indicate that the differences between the data and the initial value are statistically significant at the levels of $P<0.05$, $P<0.01$ and $P<0.001$, respectively. Each data is presented in terms of mean ± standard error (4 animals).

These figures indicate that the Compound developed a tendency toward intraocular pressure decrease even at 0.0001% and, at 0.001% and higher concentrations, produced statistically significant intraocular pressure decrease in a concentration-dependent manner. In each concentration, the intraocular pressure lowering effect was maximal at 2 hours after administration. At the concentration of 0.01%, the Compound produced a maximum intraocular pressure lowering effect; the pressure drop was as great as 8.5±1.0 mmHg (mean ± standard error for 4 animals) and statistically significant intraocular pressure decrease was noted even at 8 hours after administration.

Figure 4:
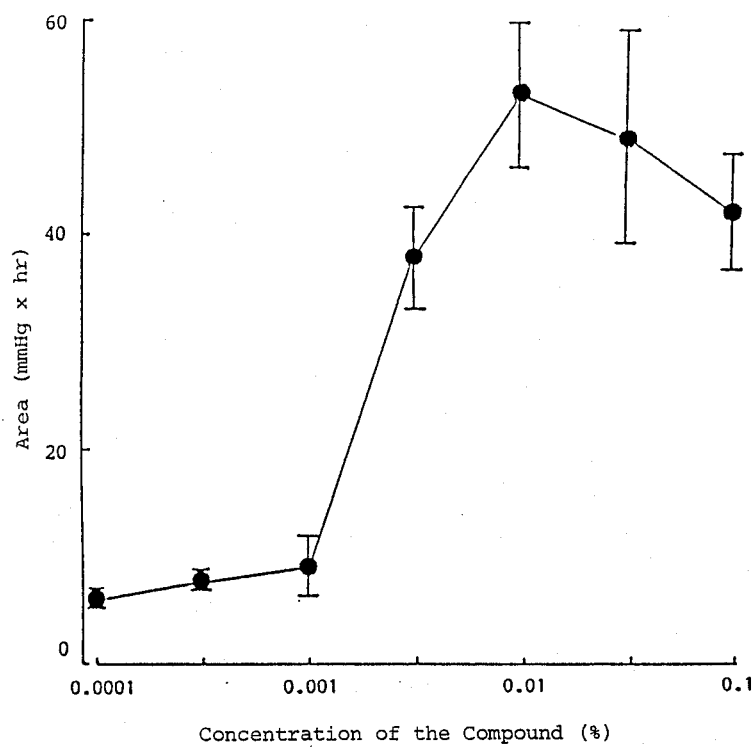
FIG. 4 shows the dose-response curve derived from the results obtained in the test example.

A dose-response curve was constructed based on the results shown in FIGS. 1–3 (FIG. 4). Thus, the area between the base line set at the initial intraocular pressure and the intraocular pressure curve after administration of the Compound (for the period of hours 0–8) was plotted along the ordinate and the concentration of the Compound along the abscissa. As a result, it became apparent that the Compound exhibits concentration-dependent intraocular pressure-lowering activity in the concentration range of up to 0.01%.

As the pupil size measurement results given in Table 1 indicate, the Compound had no influence on the pupil size.

TABLE 1

| Concentration (%) of the Compound (%) | Influence of the Compound on the pupil size Pupil size (mm ± S. E., n = 4) | | | | | | |
|---|---|---|---|---|---|---|---|
| | 0 hour | 0.5 hour | 1 hour | 2 hours | 4 hours | 6 hours | 8 hours |
| 0.0001 A | 5.00 ± 0.71 | 5.00 ± 0.71 | 5.00 ± 0.41 | 4.87 ± 0.63 | 4.87 ± 0.63 | — | — |
| V | 5.12 ± 0.41 | 5.00 ± 0.41 | 5.25 ± 0.29 | 5.12 ± 0.48 | 5.12 ± 0.48 | (Note) | |
| 0.0003 A | 4.75 ± 0.50 | 4.75 ± 0.50 | 4.87 ± 0.48 | 4.87 ± 0.48 | 4.87 ± 0.25 | — | — |
| V | 4.62 ± 0.25 | 4.87 ± 0.48 | 4.87 ± 0.25 | 4.87 ± 0.25 | 4.87 ± 0.25 | | |
| 0.001 A | 4.75 ± 0.29 | 4.50 ± 0.41 | 4.62 ± 0.25 | 4.62 ± 0.25 | 4.62 ± 0.25 | — | — |
| V | 4.62 ± 0.25 | 4.62 ± 0.48 | 4.62 ± 0.25 | 4.62 ± 0.25 | 4.62 ± 0.25 | | |
| 0.003 A | 4.75 ± 0.29 | 4.87 ± 0.48 | 4.75 ± 0.29 | 4.75 ± 0.29 | 4.75 ± 0.65 | 5.12 ± 0.48 | 5.00 ± 0.41 |
| V | 4.75 ± 0.29 | 4.87 ± 0.25 | 4.75 ± 0.29 | 4.75 ± 0.29 | 4.75 ± 0.65 | 5.12 ± 0.48 | 5.00 ± 0.41 |
| 0.01 A | 4.25 ± 0.29 | 4.25 ± 0.29 | 4.25 ± 0.29 | 4.62 ± 0.48 | 4.25 ± 0.29 | 4.25 ± 0.29 | 4.62 ± 0.48 |
| V | 4.37 ± 0.25 | 4.25 ± 0.29 | 4.25 ± 0.29 | 4.50 ± 0.41 | 4.25 ± 0.29 | 4.12 ± 0.25 | 4.75 ± 0.29 |
| 0.03 A | 4.12 ± 0.25 | 4.12 ± 0.25 | 4.00 ± 0.00 | 4.25 ± 0.29 | 4.62 ± 0.48 | 4.37 ± 0.48 | 4.62 ± 0.25 |
| V | 4.12 ± 0.25 | 4.37 ± 0.25 | 4.12 ± 0.25 | 4.25 ± 0.29 | 4.37 ± 0.48 | 4.25 ± 0.29 | 4.62 ± 0.25 |
| 0.1 A | 4.50 ± 0.41 | 4.50 ± 0.41 | 4.37 ± 0.25 | 4.62 ± 0.48 | 4.50 ± 0.41 | 4.62 ± 0.48 | 4.50 ± 0.41 |
| V | 4.75 ± 0.87 | 4.37 ± 0.48 | 4.50 ± 0.58 | 4.62 ± 0.48 | 4.50 ± 0.58 | 4.75 ± 0.29 | 4.50 ± 0.58 |

Note:
Not measured.
A = the Compound; V = base composition (phosphate buffer)

Figure 5:
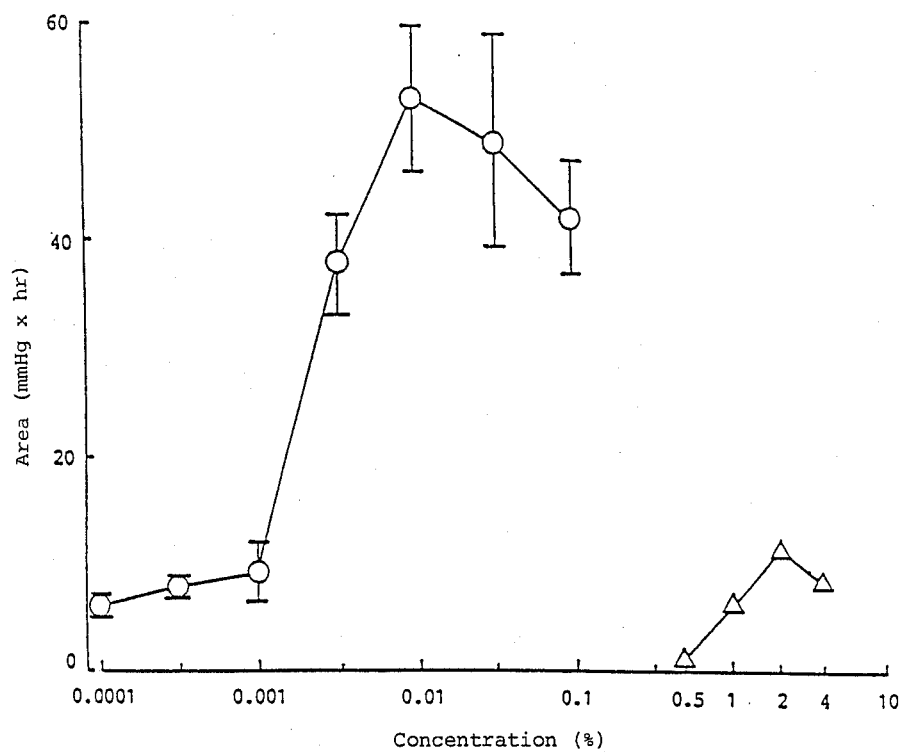
FIG. 5 shows the dose-response curve for the compound and salbutamol.

For comparison, salbutamol, which is also a beta-stimulator, was tested in the same manner. The dose-response curve for salbutamol is shown in FIG. 5 in comparison with that for Compound. The data indicated by open circles are for the Compound and those by open triangles are for salbutamol.

It was thus established that the Compound produces by far more potent intraocular pressure lowering effect in lower concentrations as compared with salbutamol.

Accordingly the possibility of tolerance development for the Compound is considered to be less and slight.

| Dosage Form Example 1 (Eye-drops) | |
|---|---|
| The Compound | 0.01 g |
| Disodium phosphate | 0.26 g |

| Dosage Form Example 1 (Eye-drops) | |
| --- | --- |
| Monosodium phosphate | 0.12 g |
| Sodium chloride | 0.65 g |
| Benzalkonium chloride | 0.005 g |
| Sodium hydroxide | Sufficient quantity |
| Sterile purified water | Sufficient quantity |
| Total | 100 ml |

The above ingredients were made up into eye-drops in the conventional manner, the pH being adjusted to 7.0. and pasteurized.

| Dosage Form Example 2 (Eye-ointment) | |
| --- | --- |
| The Compound | 0.01 g |
| White petrolatum | Sufficient quantity |
| Total | 100 g |

The above ingredients were made up into an eye ointment in the conventional manner and pasteurized.

What is claimed is:

1. An intraocular pressure lowering eye drop composition comprising:
as an active ingredient, a compound of the formula

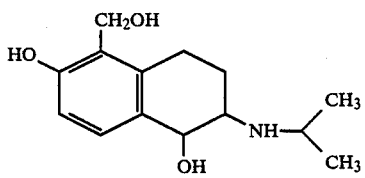

or a pharmaceutically acceptable salt thereof in an amount sufficient to lower intraocular pressure;
a preservative selected from the group consisting of parahydroxybenzoic acid esters, benzyl alcohol, para-chloro-meta-xylenol, chlorocresol, phenetyl alcohol, sorbic acid, sorbic acid salts, thimerosal and benzalkonium chloride;
a buffer;
an isotonizing agent; and,
a chelating agent.

2. A composition according to claim 1, wherein the compound or its salt is present in the composition in an amount of from 0.0001-1%.

3. An intraocular pressure lowering eye ointment composition comprising:
as an active ingredient, a compound of the formula

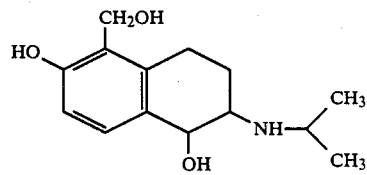

or a pharmaceutically acceptable salt in an amount sufficient to lower intraocular pressure; and
an eye ointment base.

4. A composition according to claim 3 wherein the compound or its salt is present in the composition in an amount of from 0.0001-1%.

5. A method for the treatment of high intraocular pressure in a mammal, which comprises administering topically to the eye of a mammal a pharmaceutical composition, said composition comprising an amount of a coumpound of the formula

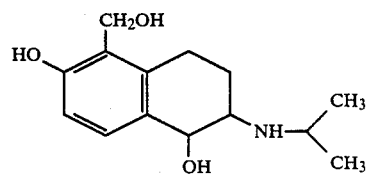

or its pharmaceutically acceptable salt in an amount sufficient to lower intraocular pressure.

6. A method according to claim 5, wherein the compound or its pharmaceutically acceptable salt is present in the composition in an amount of from 0.0001-1%.

* * * * *